United States Patent
Fedyna (10) Patent No.: US 10,765,620 B2
(45) Date of Patent: Sep. 8, 2020

(54) ORGANIC FOAMING SOAP COMPOSITION AND DISPENSER

(71) Applicant: Got Green? LLC, Reading, PA (US)

(72) Inventor: Eileen E. Fedyna, Reading, PA (US)

(73) Assignee: Got Green? LLC, Reading, PA (US)

(*) Notice: Subject to any disclaimer, the term of this patent is extended or adjusted under 35 U.S.C. 154(b) by 60 days.

(21) Appl. No.: 15/903,074

(22) Filed: Feb. 23, 2018

(65) Prior Publication Data
US 2019/0110978 A1    Apr. 18, 2019

Related U.S. Application Data

(60) Provisional application No. 62/571,310, filed on Oct. 12, 2017.

(51) Int. Cl.
*A61K 8/00* (2006.01)
*A61K 8/92* (2006.01)
(Continued)

(52) U.S. Cl.
CPC .......... *A61K 8/922* (2013.01); *A47K 5/16* (2013.01); *A61K 8/046* (2013.01); *A61K 8/345* (2013.01); *A61K 8/361* (2013.01); *A61Q 17/005* (2013.01); *A61Q 19/10* (2013.01); *B05B 11/0094* (2013.01); *B05B 11/3087* (2013.01); *A61K 2800/87* (2013.01)

(58) Field of Classification Search
None
See application file for complete search history.

(56) References Cited

U.S. PATENT DOCUMENTS 5,492,247 A    2/1996   Shu et al.
5,635,469 A    6/1997   Fowler et al.
(Continued)

OTHER PUBLICATIONS

AK Genena; H Hense; AS Junior; SM de Souza, "Rosemary (*Rosmarinus officinalis*)—a study of the composition, antioxidant and antimicrobial activities of extracts obtained with supercritical carbon dioxide", Food Science and Technology, Apr./Jun. 2008; 28(2): 463-469.

M. Al-Hijazeen, M. Al-Rawashdehi, "Preservative effects of rosemary extract (*Rosmarinus officinalis* L.) on quality and storage stability of chicken meat patties", Food Sci. Technol, ahead of print Epub Nov. 13, 2017.

(Continued)

*Primary Examiner* — Necholus Ogden, Jr.
(74) *Attorney, Agent, or Firm* — Carrie Stroup (57) ABSTRACT

An organic liquid soap composition; and a foam producing soap product comprising: a) a foamable organic liquid soap composition comprising the anti-microbial active ingredients of: organic shea butter; organic spearmint oil; USDA approved lime oil; organic thyme oil; and organic rosemary extract; and, b) a foam soap dispenser for dispensing the organic liquid soap composition as a premeasured amount of foaming soap, wherein the foam dispenser comprises: a recyclable plastic; a bottom front tab comprising a green color and a label indicating the composition is an organic soap. The organic soap composition may further comprise: glycerin; saponified organic coconut oil; organic olive oil; organic sunflower oil; organic jojoba oil; and organic aloe vera. And the organic soap composition has a shelf-life of about three years, and able to eradicate about 74.6% through 77.6% of the bacterial strain *Staphylococcus aureus* after at least one minute of direct contact with the composition.

21 Claims, 8 Drawing Sheets

| Test Organism | Exposure Time | CFU/mL in Test Population Control (Log$_{10}$) | CFU/mL of Survivors | Log$_{10}$ Survivors | Percent Reduction | Log$_{10}$ Reduction |
|---|---|---|---|---|---|---|
| Staphylococcus aureus (ATCC 6538) | 20 seconds | 7.8 x 105 (5.89) | 4.8 x 10$^5$ | 5.68 | 38.5% | 0.21 |
| | 1 minute | | 1.98 x 10$^5$ | 5.30 | 74.6% | 0.59 |
| | 2.5 minutes | | 1.81 x 10$^5$ | 5.26 | 76.8% | 0.63 |
| | 5 minutes | | 1.75 x 10$^5$ | 5.24 | 77.6% | 0.65 |

(51) Int. Cl.
  *A61K 8/34* (2006.01)
  *A61K 8/04* (2006.01)
  *B05B 11/00* (2006.01)
  *A61Q 19/10* (2006.01)
  *A47K 5/16* (2006.01)
  *A61Q 17/00* (2006.01)
  *A61K 8/36* (2006.01)

(56) References Cited

U.S. PATENT DOCUMENTS

| | | | |
|---|---|---|---|
| 6,068,162 A | 5/2000 | De Winter et al. | |
| 6,390,329 B1 | 5/2002 | Maddox | |
| 6,409,050 B1 | 6/2002 | Ophardt et al. | |
| 7,281,643 B2 | 10/2007 | Lin | |
| 7,838,477 B2 | 11/2010 | Wenzel et al. | |
| 8,091,739 B2 | 1/2012 | Ophardt et al. | |
| 8,113,388 B2 | 2/2012 | Ophardt et al. | |
| 8,308,027 B2 | 11/2012 | Law et al. | |
| 8,413,852 B2 | 4/2013 | Ophardt et al. | |
| 8,991,657 B2 | 3/2015 | Ciavarella et al. | |
| 9,439,841 B2 | 9/2016 | Wegner et al. | |
| 9,447,366 B2 | 9/2016 | McCarthy et al. | |
| 2013/0119083 A1 | 5/2013 | Ophardt et al. | |
| 2015/0005215 A1* | 1/2015 | McCarthy | C11D 9/262 510/129 |
| 2015/0152359 A1* | 6/2015 | McCarthy | C11D 3/382 510/462 |
| 2017/0027390 A1* | 2/2017 | Maercovich | A47K 5/1217 |

OTHER PUBLICATIONS

Y. Shahbazi, "Chemical Composition and In Vitro Antibacterial Activity of *Mentha spicata* Essential Oil against common Food-Borne Pathogenic Bacteria", J Pathog. 2015; 1-5.

Y. Shahbazi, N. Karami, N. Shavisi, "Effect of *Mentha spicata* essential oil on chemical, microbial, and sensory properties of minced camel meat during refrigerated storage", Feb. 2018; 38(1): 1-7.

K. Sowndhararajan, S. Kim, "Influence of Fragrances on Human Psychophysiological Activity: With Special Reference to Human Electroencephalographic Response", Sci Pharm. 2016; 84(4): 724-752.

S.S. Bhandari, M.P. Kabrab, "To evaluate anti-anxiety activity of thymol", Journal of Acute Disease, 2014, 3(2): 136-140.

CM Priestley, EM Williamson, KA Wafford, and DB Sattelle, "Thymol, a constituent of thyme essential oil, is a positive allosteric modulator of human GABAA receptors and a homo-oligomeric GABA receptor from *Drosophila melanogaster*", Br J Pharmacol. Dec. 2003; 140(8): 1363-1372.

T. Lockette, "Florida researchers use essential oil as earth-friendly pesticide", SouthEast FarmPress, Apr. 21, 2004.

EPA Red Facts, Thymol, EPA-738-F-93-010, Sep. 1993.

TM Nalawade, K Bhat, SHP Sogi, "Bactericidal activity of propylene glycol, glycerine, polyethylene glycol 400, and polyethylene glycol 1000 against selected microorganisms," J Int Soc Prev Community Dent. Mar.-Apr. 2015; 5(2): 114-119.

\* cited by examiner

| DILUTION (VOLUME PLATED) | Test Organism: *Staphylococcus aureus* (ATCC 6538) | | | |
|---|---|---|---|---|
| | Exposure Time | | | |
| | 20 seconds | 1 minute | 2.5 minutes | 5 minutes |
| | Number of Survivors | | | |
| $10°$ (1.00 mL) | T, T | T, T | T, T | T, T |
| $10°$ (0.100 mL) | T, T | T, T | T, T | T, T |
| $10^{-1}$ (0.100 mL) | T, T | 194, 202 | 160, 202 | 172, 178 |
| $10^{-2}$ (0.100 mL) | 58, 37 | 27, 34 | 24, 18 | 20, 21 |
| $10^{-3}$ (0.100 mL) | 3, 5 | 9, 2 | 1, 2 | 0, 1 |

T = Too Numerous to Count (>300 colonies)

FIG. 1

| Test Organism | Exposure Time | CFU/mL in Test Population Control ($Log_{10}$) | CFU/mL of Survivors | $Log_{10}$ Survivors | Percent Reduction | $Log_{10}$ Reduction |
|---|---|---|---|---|---|---|
| *Staphylococcus aureus* (ATCC 6538) | 20 seconds | 7.8 x 105 (5.89) | $4.8 \times 10^5$ | 5.68 | 38.5% | 0.21 |
| | 1 minute | | $1.98 \times 10^5$ | 5.30 | 74.6% | 0.59 |
| | 2.5 minutes | | $1.81 \times 10^5$ | 5.26 | 76.8% | 0.63 |
| | 5 minutes | | $1.75 \times 10^5$ | 5.24 | 77.6% | 0.65 |

ORGANIC FOAMING SOAP COMPOSITION AND DISPENSER

PRIORITY CLAIM

The present application claims the benefit of priority to U.S. Provisional Ser. No. 62/571,310, filed Oct. 12, 2017 by E. Fedyna, and entitled "Wholly Organic Liquid Soap Composition", the entire contents of which are hereby incorporated by reference in its entirety.

TECHNICAL FIELD

The present disclosure generally relates to anti-microbial organic hand soaps, and in particular to environmentally friendly, anti-microbial, organic plant-based compositions for use in a recyclable foaming soap dispenser.

TRADEMARKS DISCLAIMER

The product names used in this document are for identification purposes only. All trademarks and registered trademarks are the property of their respective owners.

BACKGROUND

Wholly organic liquid hand soap compositions are desirable because naturally occurring ingredients are more healthful to the human body when absorbed into the dermis and present no harmful or "toxic residual effect" within or around the bloodstream. Contrarily, non-organic, traditional soaps comprise chemicals that are harmful to both the user and the environment, such as: Triclosan, Sodium Lauryl Sulfate (SLS), Diethanolamine (DEA), Parabens, Synthetic Colors, Synthetic Fragrance, Urea, Propylene Glycol, 1,4-Dioxane, Ethyl Alcohol (Ethanol) and Benzalkonium Chloride (BAC).

Triclosan: In 2016, the Food and Drug Administration (FDA) issued a rule stating that over-the-counter consumer antiseptic wash products containing many potentially harmful antibacterial active ingredients—including triclosan and triclocarban—can no longer be marketed to consumers. These products include liquid, foam and gel hand soaps, bar soaps, and body washes. Research has shown that triclosan: alters hormone regulation in animals; contributes to the development of antibiotic-resistant germs; and is harmful to the immune system. The compositions of the present invention do not comprise triclosan, triclocarban, or any other non-organic, plant-based ingredient.

Environment: Organically derived ingredients provide not only an effective hand washing experience for the end-user, but also, provide a less toxic avenue for potential environmental hazards. Liquid hand soap compositions to date use harsh preservatives, such as formaldehyde, urea, parabens and sulfates like cocamidopropyl betaine, which can get into lakes and waterways and cause allergic reactions and derma irritation. Use of these harsh preservatives require drinking water processing facilities to remove them, resulting in more waste elimination work.

Soaps require preservatives to: help prevent microbial growth and rancidity in the soap, maintain its effectiveness, and increase the shelf-life of the soap. In the past, hand soap compositions have relied upon non-organic, chemical means of extending a soap's shelf-life because harm to the user from exposure to the chemical preservatives was not well known or understood, and because alternative non-chemical preservatives were ineffective or too costly.

For example, organic soaps have a shelf-life of 18 through 24 months, while commercial chemical soaps can be stored for up to 3 years. Additionally, Deb Soap™ and AntiBac FH Pure Foam™ chemical soap lasts up to 30 months, and castor oil-based soaps have a shelf life of approximately one-year time, and sunflower oil-based soaps have a shelf life of 3 to 6 months. When the product expires, the oils go rancid, change in odor and color (e.g. brown), become moldy and also tend to separate.

What is needed within the hand soap industry is an organic plant-based liquid or foaming soap that does not comprise any non-organic chemical preservatives, but which has strong anti-microbial properties and a shelf-life that is equivalent to, or superior to, chemical soaps; and a wall mounted soap dispenser for use with the composition, wherein the dispenser and its refillable soap cartridge are environmentally friendly, e.g. made entirely from recyclable materials.

SUMMARY

Anti-Microbial Organic Foaming Soap Compositions

Liquid hand soap compositions according to the invention can be made wholly organic with a long shelf-life because of a newly-derived combination of organic ingredients processed in certain ways. These organic blends are highly preferable because they contain a synergistic combination of "naturally occurring antibacterial agents" in addition to vitamins and minerals known to protect the skin's surface.

The various embodiments of anti-microbial, foam-able composition of the present disclosure comprise the following anti-microbial active ingredients, all of which are oils certified to USDA Organic Standards: organic shea butter; organic spearmint oil; USDA approved lime oil; organic thyme oil; and organic rosemary extract.

In an embodiment of the organic soap composition, the organic shea butter is in a range from about 0.5 weight percent to about 5% weight percent.

In an embodiment of the organic soap composition, the organic spearmint oil is in a range from about 0.42 weight percent to about 0.7 weight percent.

In an embodiment of the organic soap composition, the United States Department of Agriculture (U.S.D.A) approved lime oil is in a range from about 0.44 weight % to about 0.66 weight %.

In an embodiment of the organic soap composition, the organic thyme oil is in a range from about 0.07 weight % to about 0.11 weight %.

In an embodiment of the organic soap composition, the organic rosemary extract is in a range from about 0.01 weight % to about 0.13 weight %.

In an embodiment, the composition further comprises a base soap composition of: saponified organic coconut oil; organic olive oil; organic sunflower oil; organic jojoba oil; and organic aloe vera. In an embodiment, the composition may further comprise glycerin as a base soap ingredient, wherein the glycerin is a by-product of the manufacturing product from combining the organic essential oils with water and alkali, and then glycerin is added back into the composition.

Scented or Unscented Base Soap Composition: In an embodiment, the present disclosure comprises the base soap composition alone without the anti-microbial active ingredients, with or without at least one organic scented oil.

The compositions disclosed herein do not comprise sulfites, non-organic plant-based chemicals, or synthetic compounds. In an embodiment, the compositions are 100% organic; and another embodiment, the compositions are certified with organic ingredients, wherein all ingredients are organic, with the exception of the lime oil.

Formulations: the anti-microbial composition of the present disclosure is stored in a liquid formulation that based upon the type of soap dispenser may be dispensed as a liquid (e.g. pump dispenser) or a foam (foaming dispenser). In smaller quantities, the anti-microbial composition is left on the skin as a foamed or liquid "hand sanitizer" that is absorbed into the skin without leaving a sticky or tacky residue.

Shelf-life: the anti-microbial composition of the present disclosure has a shelf-life of about three years, which is equivalent to non-organic liquid and foaming soaps.

Anti-microbial: the compositions of the present disclosure exhibit anti-microbial properties.

Foaming Soap Dispenser

In an embodiment, the entire dispenser housing, and the refillable soap cartridge are made entirely of recyclable material, such as recyclable plastic material that comprises at least one of: polyethylene terephthalate (PET); high density polyethylene (HDPE); polyvinyl chloride; low density polyethylene (LDPE); polypropylene (PP); polystyrene (PS); and ABS In an embodiment, the dispenser is manually pump activated.

In another embodiment, the dispenser is automatic (i.e. touchless) wherein the user activates a sensor to trigger the release of the soap, but without touching the dispenser.

In all embodiments, the soap dispenser comprises markings to indicate that the soap is an environmentally friendly, organic plant-based, such as: a "got green?®" trademark; a Got Green® website address that lists the compositions' anti-microbial active ingredients; a green or partially green colored leaf on the front of the dispenser; and/or a green push tab on the bottom front of the dispenser.

Foam Producing Soap Product

In an embodiment, of the present disclosure comprises a foam producing soap product comprising: a) a foam-able organic liquid soap composition comprising the anti-microbial active ingredients of: organic shea butter; organic spearmint oil; USDA approved lime oil; organic thyme oil; and organic rosemary extract; and, b) a foam soap dispenser for dispensing the organic liquid soap composition as a premeasured amount of foaming soap, wherein the foam dispenser comprises: a recyclable plastic; a bottom front tab comprising a green color and a front label indicating the composition is an organic soap.

In an embodiment of the foam producing soap product, the foam soap dispenser is a manual soap dispenser, and the bottom front tab is green colored and comprises a manually operable pumping means.

In an embodiment of the foam producing soap product, the foam soap dispenser further comprises a liquid soap filled reservoir that is operatively connected to the pumping means for supplying the organic soap composition to the dispenser via a vertically mounted tube extending between the reservoir and a dispenser nozzle connected to a close/open valve.

In an embodiment of the foam producing soap product, the organic soap composition further comprises the base soap composition ingredients of: saponified organic coconut oil; organic olive oil; organic sunflower oil; organic jojoba oil; and organic aloe vera.

In an embodiment of the foam producing soap product, the organic soap composition further comprises glycerin that is produced during the process of making the base soap composition, that is remixed into the composition. In an embodiment of the foam producing soap product, the shelf-life of the organic soap composition is about three years.

In an embodiment of the foam producing soap product, the organic soap composition is able to eradicate about 74.6% through 77.6% of the bacterial strain *Staphylococcus aureus* after at least one minute of direct contact with the composition.

DETAILED DESCRIPTION OF EXEMPLARY EMBODIMENTS

A detailed description of a preferred embodiment and process is provided herein. It is to be understood, however, that the invention may be embodied in various forms and processed using other methods. Therefore, specific details disclosed herein are not to be interpreted as limiting, but rather as a basis for patent claims and as a representative basis for teaching one skilled in the art to employ the present invention in virtually any appropriately detailed system, structure or manner.

As used herein, the term "essential oil" refers to an essential oil as a product made by distillation with either water or steam or by mechanical processing of citrus rinds or by dry distillation of natural materials. Following the distillation, the essential oil is physically separated from the water phase. For an essential oil to be a true essential oil, it must be isolated by physical means only. The physical methods used are distillation (steam, steam/water and water) or expression (also known as cold pressing, a unique feature for citrus peel oils). There is one other method of oil isolation specific to a very limited number of essential oil plants. This is a maceration/distillation. In the process, the plant material is macerated in warm water to release the enzyme-bound essential oil.

As used herein, the term "by weight" or "wt. %" refers to the amount of the stated composition ingredient as a percentage of the entire composition: base soap ingredients (Table 2), or base soap ingredients plus scented essential oils, or base soap ingredients plus anti-microbial active ingredients (Table 1). For example, if the entire foaming soap composition disclosed herein has by weight 100 grams, then the composition comprises, in an embodiment, organic rosemary extract from 0.01 grams to 0.1 grams.

As used herein, the term "about" means five percent plus or minus the stated value.

Wholly organic liquid hand soap compositions according to the invention are the first "organically formulated" hand soaps to be crafted without the use of chemically altered, man-made preservation methods. The natural preservation methods described herein extend the duration of shelf life beyond that of what many inorganic preservatives can achieve. These compositions maintain stability with use the of rosemary organic extract and the process used to incorporate it into the compositions.

In accordance with 7 CFR § 205.301, the soap compositions of the present disclosure are "made with organic", which contains (by weight, excluding water and salt) at least 70 percent to 94 percent organically produced ingredients. The soap compositions of the present disclosure are also certified to USDA Organic Standards.

As used herein, the term "anti-microbial active" and "active" are used interchangeably herein and refers to the soap composition ingredients that act in an unexpected synergistic manner (e.g. Table 1 ingredients) to render the soap composition able to reduce at least one type of bacterial infection or presence on the user's skin, such as a gram positive bacterial infection.

It is important to note in this context there is a distinction between pure rosemary essential oil and that of rosemary extract as a plant extract. Liquid that is distilled or separated from plant extract is commonly referred to as the "plant essence" and the minimal amount of "volatile liquid" left behind is the essential oil. Rosemary extract specifically is very different from "rosemary essential oil," as the extract has a very high level of antioxidants when absorbed or ingested. Antioxidants are known to fight "free-radicals"; therefore, when the extract is used as a method of preservation, it prevents the breakdown of natural products such as the wholly organic liquid hand soap compositions described herein. Rosemary oil, on the other hand, is used for a variety of medicinal purposes and does not contain the preservation level of an "extract" (e.g. see List of References infra (1, 2)).

The rosemary extract is added to the blended oils prior to the soap composition being mixed and created. This process results in doubling shelf-life by using the antioxidant properties of the rosemary extract to slow the breakdown of the other natural ingredients in the soap composition.

One preferred liquid hand soap composition according to the invention contains organic thyme oil, spearmint oil, and rosemary extract; and USDA approved lime oil; and shea butter.

Thymol wards off gram-positive bacteria on the skin's surface. This particular anti-microbial active oil also aids to create a residual barrier of protection on the hand's surface to prevent the spread of germs and parasitic matter, such as scabies and lice, from one person to another. Thyme essential oil also contains naturally occurring antibacterial properties that help prevent bacteria build-up in the sink drain by coating the metal pipe on the way down. In the future, this aspect will help prevent bacterial *C. Diff* sewage back-up, which is a current phenomenon occurring in hospital wash sinks.

Spearmint oil, certified to USDA Organic Standards, is used to mask the scent of thymol used in the composition, and provides an energized "uplifting" aroma. Spearmint also has natural antiseptic properties (due to the presence of menthol, myrcene and caryophyllene) that are effective against bacteria (3, 4). Additionally, both thymol and spearmint have been studied scientifically to stimulate the nerves and brain function, which is beneficial for users. A main factorial of this is thymol's ability to have an instant effect on brain activity, which has been revealed by monitoring brain activity via electroencephalograms. The mood encouraging nature of the composition is also being explored (5, 6, 7).

USDA approved lime oil is used to create a pleasing "spearmint-lime" scent. This also provides a novel twist on the scent. Just like the previously mentioned organic oils, lime oil also contains antiseptic, antiviral and antibacterial properties. A spearmint-lime scent appeals to both fans of citrus and of mint. Due to the natural "spearmint-lime" scent, which disperses in the air with the foaming dispenser disclosed herein, other air fresheners are not required. Additional organic plant-based scents may be added to the composition. And, the composition may be scented, or unscented.

Shea butter is used as a moisturizer, which helps the skin retain moisture after hand washing, but when utilized minimally as a "leave-on", helps transport the formula into the deeper layers of the derma and turn the once "wet" formula into a soft, silky feel after several minutes time. Additionally, due to the shea butter's cinnamic acid, it works as an anti-inflammatory and is found to reduce skin inflammation. Thus, the compositions of the present disclosure can be used to relieve the "aches and pains" symptoms of disorders and conditions, such as carpal tunnel syndrome and rheumatoid arthritis, by inducing a natural anti-inflammatory effect. Some previous hand soap compositions, comprise pharmaceutically-produced non-steroidal anti-inflammatory drugs (NSAIDS) that are used as the inorganic means for anti-inflammatory properties listed in the compositional makeup. This is not only dangerous, but due to the fact that a large amount of pharmaceutically produced NSAIDS contain formaldehyde and/or, this raises the risk of increased "premature" illness rates, e.g. nausea, headaches, respiratory problems and cancer (see U.S. Pat. No. 5,635,469 A that issued to T J Fowler on Jun. 3, 1997).

Glycerin: in additional embodiments of the present disclosure, glycerin, which is a by-product of the manufacturing process using plant oils, is added back-into the final soap composition to produce a milder hand soap with enhanced moisturizing effect. Glycerin is a humectant, meaning that it attracts water. When glycerin is applied to the skin as an optional ingredient of the composition, it seals in moisture that might otherwise escape. Glycerin may also contribute to the anti-microbial activity of the soap composition (10).

Anti-bacterial Active Ingredients: A preferred version of the composition comprises the following combination of anti-microbial active ingredients: organic shea butter; organic spearmint oil; USDA approved lime oil; organic thyme oil; and organic rosemary extract. In another embodiment, glycerin is an additional ingredient.

The various compositions of the present disclosure exhibit strong, anti-microbial effects due to the unexpected synergistic effects of combining the ingredients of Table 1, which alone have some anti-microbial properties.

In an embodiment, the organic shea butter is in a range from about 0.5% (by weight) to about 5% (by weight), and more preferably from about 0.6073 wt. % to about 1.1021 wt. %.

In an embodiment, the organic spearmint oil is in a range from about 0.42 wt. % to about 0.7 wt. %, and more preferably from about 0.5241 wt. % to about 0.5911 wt. %.

In an embodiment, the USDA approved lime oil is in a range from about 0.44 wt. % to about 0.66 wt. %, and more preferably from about 0.4992 wt. % to about 0.5630 wt. %.

In an embodiment, the organic thyme oil is in a range from about 0.07 wt. % to about 0.11 wt. %, and more preferably from about 0.0873 wt. % to about 0.0985 wt. %.

In an embodiment, the organic rosemary extract is in a range from about 0.01 wt. % to about 0.13 wt. %, and more preferably from about 0.01 wt. % to about 0.10 wt. %.

Table 1 provides a list of the weight percent range for each anti-microbial active ingredient within one exemplary foaming soap composition that is a preferred embodiment.

TABLE 1

| Antimicrobial Active Ingredients | Exemplary Range of Weight Percent |
|---|---|
| Organic Shea Butter | about .50 wt. % to about 5.0 wt. % |
| Organic Spearmint Oil | about .5241 wt. % to about .5911 wt. % |
| USDA approved Lime Oil | about .4992 wt. % to about .5630 wt. % |
| Organic Thyme Oil | about .0873 wt. % to about .0985 wt. % |
| Organic Rosemary Extract | about .01 wt. % to about .13 wt. % |

Base Soap Ingredients: the remainder of the foaming soap composition of the various embodiments of the present disclosure further comprises other organic oils, such as: saponified organic coconut oil; organic olive oil; organic sunflower oil; organic jojoba oil; and organic aloe vera (see Table 2).

Due to the anti-microbial properties of the composition of Table 1, it can also be used as a leave on hand sanitizer when dispensed in smaller doses, wherein the composition is absorbed into the skin without leaving a sticky residue on the user's skin.

Unscented Versus Scented Soap

The various soap compositions of the present disclosure comprise the base soap ingredients of Table 2, which is an unscented version of the soap composition.

| Base Soap Ingredients | Exemplary Range of Weight Percent |
|---|---|
| Saponified Organic Coconut Oil | about 15 wt. % to about 75 wt. % |
| Saponified Organic Olive Oil | about 1.0 wt. % to about .20 wt. % |
| Saponified Organic Sunflower Oil | about 1.0 wt. % to about .20 wt. % |
| Saponified Organic Jojoba Oil | about 1.0 wt. % to about .20 wt. % |
| Organic *Aloe Vera* | about .01 wt. % to about .20 wt. % |
| Glycerin (optional) | about 1 wt. % to about 15 wt. % |

Scented soap: The soap composition of the present disclosure may further comprise at least one of the following oils, or any combination thereof, to scent the soap: orange essential oil, lemon essential oil, lime essential oil, citrus blend essential oil, kiwi oil, strawberry essential oil, raspberry essential oil, elderberry essential oil, juniper berry essential oil, cranberry essential oil, pomegranate essential oil, vanilla essential oil, lemongrass essential oil, rosemary essential oil, patchouli essential oil, thyme essential oil, spearmint essential oil, peppermint essential oil, wintergreen essential oil, cinnamon bark and leaf essential oil, sage essential oil, basil essential oil, sweet basil essential oil, pine blend essential oil, frankincense essential oil, ginger essential oil, mandarin essential oil, tangerine essential oil, grapefruit essential oil, floral fragrance, lavender essential oil, rose essential oil, gardenia essential oil, geranium essential oil, sweet marjoram oil, nutmeg essential oil, bergamot essential oil, cardamom essential oil, chocolate fragrance oil, and coconut fragrance oil.

Method of Making the Foaming Organic Soap

The organic liquid and/or foaming hand soap compositions according to the various embodiments of the present disclosure are made according to the following exemplary method.

Base Soap: The process begins with pre-mixing the rosemary extract with the non-anti-microbial active oils prior to its addition into the whole soap composition. In an embodiment, the base soap composition of Table 2 is utilized to make the unscented soap (one embodiment), to which at least one scented oil may be added (second embodiment), or to which the naturally occurring anti-bacterial ingredients of Table 1 are added (third embodiment).

For all embodiments, the rosemary extract and the base soap ingredients of Table 2, such as coconut and other plant-based oils (i.e. saponified organic coconut oil; organic olive oil; organic sunflower oil; organic jojoba oil; and organic aloe vera) are pumped into kettles. Then fluids (i.e. water at about 81 wt. %) are combined along with alkali (e.g. potassium hydroxide at about 3.48 wt. %) into the kettles. Following this, the certified base soap ingredients comprising the organic oils of Table 2, water and alkali combine to form liquid soap and glycerin. To create a "milder" soap, the glycerin is added back into the composition. This differs largely from generic, chemically-created liquid hand soap because they do not add the glycerin back into the finalized product during production. Failing to take this extra step results in a harsh hand soap formulation that can be very drying and irritating to skin.

After the cooking process has completed (e.g. duration of heating about 4 to 5 hours up to 200 degrees Fahrenheit), the base soap composition (with glycerin, or with the glycerin removed) is then pumped into tanks and cooled. The anti-microbial active organic oil ingredients (e.g. see Table 1 for exemplary weight percent amounts of each anti-microbial active ingredient) are then added into to the base soap composition, which creates the natural effect of the antiseptic and preserving properties in the hand soap Formulations and Methods of Use Formulations: the anti-microbial compositions of the present disclosure are stored in a liquid formulation that based upon the type of soap dispenser may be dispensed as a liquid (e.g. pump dispenser—e.g. see FIG. 1) or a foam (foaming dispenser—e.g. see FIGS. 2-7). In smaller quantities, the anti-microbial composition is left on the skin as a foamed or liquid "hand sanitizer" that is absorbed into the skin without leaving a sticky or tacky residue.

The compositions of the present disclosure are primarily used to reduce the amount and proliferation of pathogens: microbes, germs, parasites, viruses, fungi, bacteria on the user's hands, although all skin epidermis can also be sterilized.

In an embodiment, the compositions of the present disclosure should not cause user immune response resistance to pathogens, e.g. bacterial, viral, etc.

The compositions of the present disclosure can also be used as an anti-inflammatory and a topical analgesic due to the shea butter's cinnamic acid.

The compositions of the present disclosure can also be used to moisturize and deeply condition dry skin due to the shea butter.

The compositions of the present disclosure can also be used as a room air freshener because the plant oils in the anti-microbial active ingredients eradicate the airborne bacteria.

The compositions of the present disclosure can also be used as a bug repellent, such as to deter mosquitoes and ticks due to the thyme oil (8, 9).

Experimental Data Demonstrating Anti-Microbial Activity

The anti-microbial properties of the composition of Table 1 were tested against the bacterial strain *Staphylococcus aureus*, with the American Type Culture Collection identifier (ATCC 6538).

Experimental Design: a suspension of the test organism *Staphylococcus aureus* (ATCC 6538) was exposed to the test substance of the composition of Table 1 for the specified exposure times. After exposure, an aliquot of the suspension was transferred to neutralizer (D/E Neutralizing Broth) and was assayed for survivors. Appropriate culture purity, neutralizer sterility, test population, and neutralization confirmation controls were performed.

Figure 1:
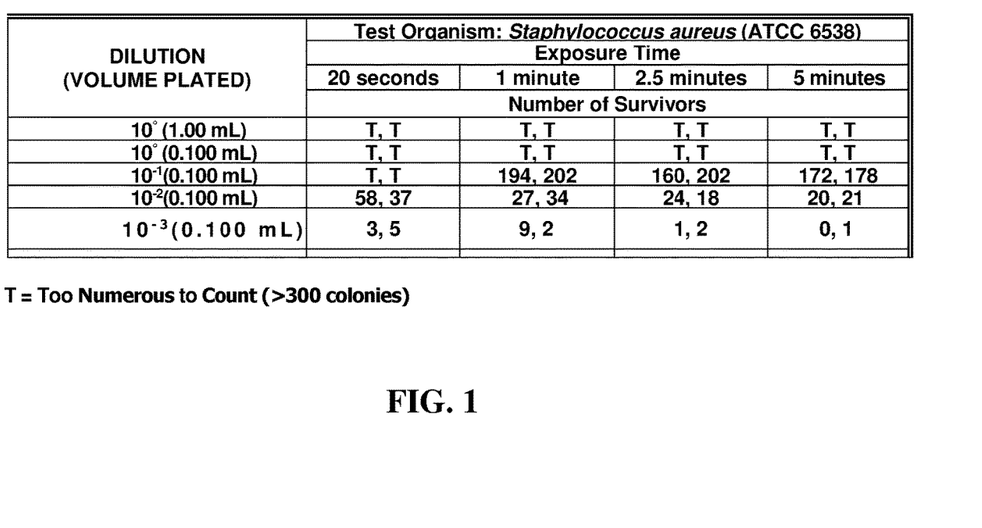
FIG. 1 is a table of experimental results demonstrating that the maximum eradication of the bacteria *Staphylococcus aureus* (ATCC 6538) occurred with exposure between one minute and five minutes of the composition of Table 1 to the bacterial culture of Table 2, and wherein the dilution of bacteria is in the amount of at least $10^{-1}$ (0.100 mL) to $10^{-3}$ (0.100 mL).
Figure 2:
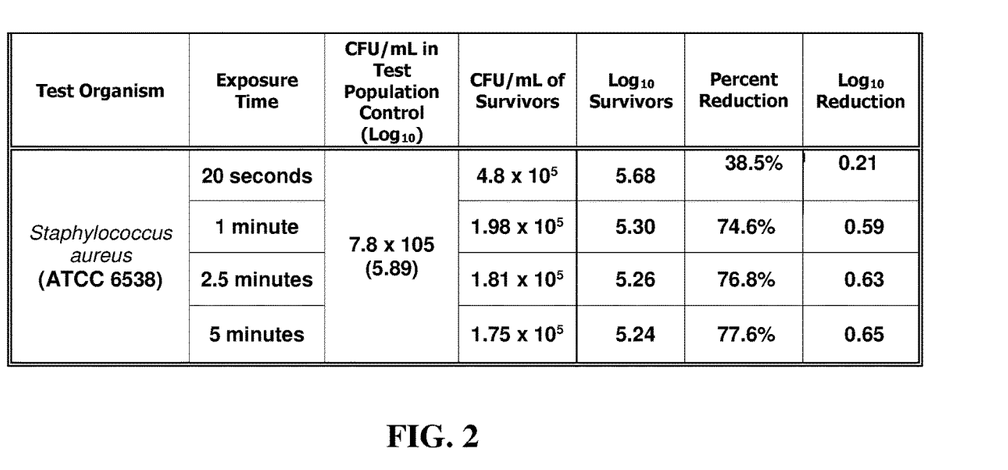
FIG. 2 is a table of experimental results demonstrating that exposure of the composition of Table 1 to the bacterial culture of Table 2 for at least one minute resulted in 74.6% through 77.6% eradication of all of the bacterial colony forming units within the culture.

Results: As illustrated in FIGS. 1 and 2, GOT GREEN SOAP (Batch # OR-73231) ready to use, demonstrated a 38.5% (0.21 $\log_{10}$) reduction of *Staphylococcus aureus* (ATCC 6538) survivors following a 20 second exposure time, a 74.6% (0.59 log10) reduction of *Staphylococcus aureus* (ATCC 6538) survivors after a 1 minute exposure time, a 76.8% (0.63 $\log_{10}$) reduction of *Staphylococcus aureus* (ATCC 6538) survivors after a 2.5 minute exposure time and a 77.6% (0.65 $\log_{10}$) reduction of *Staphylococcus aureus* (ATCC 6538) survivors after a 5 minute exposure when tested at ambient temperature (20° C.).

Per FIG. 1, the maximum eradication of the bacteria *Staphylococcus aureus* (ATCC 6538) occurred with exposure of the composition of Table 1 to bacterial culture of Table 2, wherein the dilution of bacteria is in the amount of 0.001 bacteria colonies per 0.100 milliliters of the bacterial culture.

TABLE 3

| Test Organism | ATCC # | Growth Medium | Incubation Parameters |
|---|---|---|---|
| *Staphylococcus aureus* | 6538 | Tryptic Soy Agar + 5% Sheep Blood | 35-37° C., aerobic |

And as illustrated in FIG. 2, exposure of the composition of Table 1 to the bacterial culture of Table 3 for at least one minute resulted in 74.6% through 77.6% eradication of all of the bacterial colony forming units within the culture.

Shelf-Life Extended

Normally, organic liquid soaps have a short shelf-life of about one year because of the lack of a preservative. A sunflower oil-based liquid soap has an even shorter shelf-life of about 3-6 months. Chemical liquid hand soaps with artificial preserving agents have a shelf-life of about two years. Yet, the anti-microbial compositions of the present disclosure have a shelf-life of about three years, which is due in part to the unexpected synergistic effect of the combination of the oils of Table 1 for preserving the soap composition, especially the rosemary extract.

The organic rosemary extract is added to the base soap composition of Table 2 prior to the base soap composition being mixed, heated, and cooled. This process results in doubling shelf-life by using the antioxidant properties of the rosemary extract to slow the breakdown of the other natural ingredients in the soap composition.

Foam Producing Soap Product

The present disclosure further comprises a foam producing soap product comprising: a) a foam-able organic liquid soap composition comprising the anti-microbial active ingredients of Table 1: organic shea butter; organic spearmint oil; USDA approved lime oil; organic thyme oil; and organic rosemary extract; and, b) a foam soap dispenser for dispensing the organic liquid soap composition as a premeasured amount of foaming soap, wherein the foam dispenser comprises: a recyclable plastic; a bottom front tab comprising a green color and a front label indicating the composition is an organic soap. The foam-able organic liquid soap composition further comprises the base soap composition of Table 2.

In another embodiment, the foaming soap composition comprises the base soap composition of Table 2, and with or without the addition of at least one scented oil; and without all of the oils of Table 1.

Cost Effective: The foam producing soap product of FIGS. 6-9 with the composition of Table 1 has been demonstrated to be more cost effective than commercial chemical soaps, due to the amount of soap dispensed with each pump, the higher viscosity and the longer shelf-life of the organic soap, and the volume of the results in significant cost savings. Table 4 comprising a study conducted in the King of Prussia (KOP) Mall comparing use of GOJO™ Foam Hand wash (Type: Antibacterial) to the present disclosure's Got Green? soap. Results: GOJO dispensers lasted about one week in public restrooms, whereas Got Green? dispensers lasted for about 3 weeks in the woman's restroom and about 1 month in the men's restroom. These was thus a $11.37 savings using Got Green? per case (case equals 4 fills) versus GOJO™.

TABLE 4

| Company | No. of Fills | Price | Milliliters | Time Factor | Overall Cost |
|---|---|---|---|---|---|
| GOJO ™ | 1 | $12.85 | 1,250 | 1.0 | $10.28 |
| Got Green? ® | 1 | $22.31 | 1,000 | 3.0 | $7.44 |

Liquid and Foaming Soap Dispensers

The soap compositions for the present disclosure are housed in a soap dispenser that pumps out the soap in a liquid form, or as a foam, based upon the mechanical components of the dispenser.

The dispensers of the present disclosure are also either automatic, so that the user does not need to touch the dispenser (e.g. FIG. 3), or manual (e.g. FIGS. 4-9), where the user pushes inward on a bottom green colored tab.

In all embodiments of the present disclosure, the soap composition is housed within a dispenser that comprises markings to indicate that the soap is an environmentally friendly, organic plant-based soap, such as: a "got green?®" trademark 120 (Registration No. 4904158, issued on Feb. 23, 2016), with a green color of pantone shade 2427 C; and a green colored lower push-tab 140-146 on the bottom front of the dispenser. The push-tab in all embodiments is colored green per the dispenser color mark registration of FIGS. 6-9, 146, with the color mark application number 87457091, filed on May 19, 2017 by Fedyna, which claims pantone green color 2424 XGC, or 2424.

The front of the soap dispenser may further comprise a leaf-shaped clear or opaque window that displays the level of the soap composition remaining within the dispenser (e.g. FIGS. 3-5, 130).

The front of the soap dispenser may further comprise the Got Green® website address 150 that lists, for example, the composition's anti-microbial active ingredients, as well as, the intellectual property protection of the composition. The website may further list the intellectual property protection of the dispenser of FIGS. 3-6, such as design patent numbers. And the dispensers may have markings indicating the soap composition is "Plant-Based Foam Soap" as illustrated in FIG. 4, 163; or markings of "Plant-Based Foam Hand Soap", as illustrated in FIGS. 6-9, 162. Other decorative markings may also be added to the dispenser, such as a colored border on the front of the dispenser (e.g. FIG. 4, gold border 170).

Figure 3:
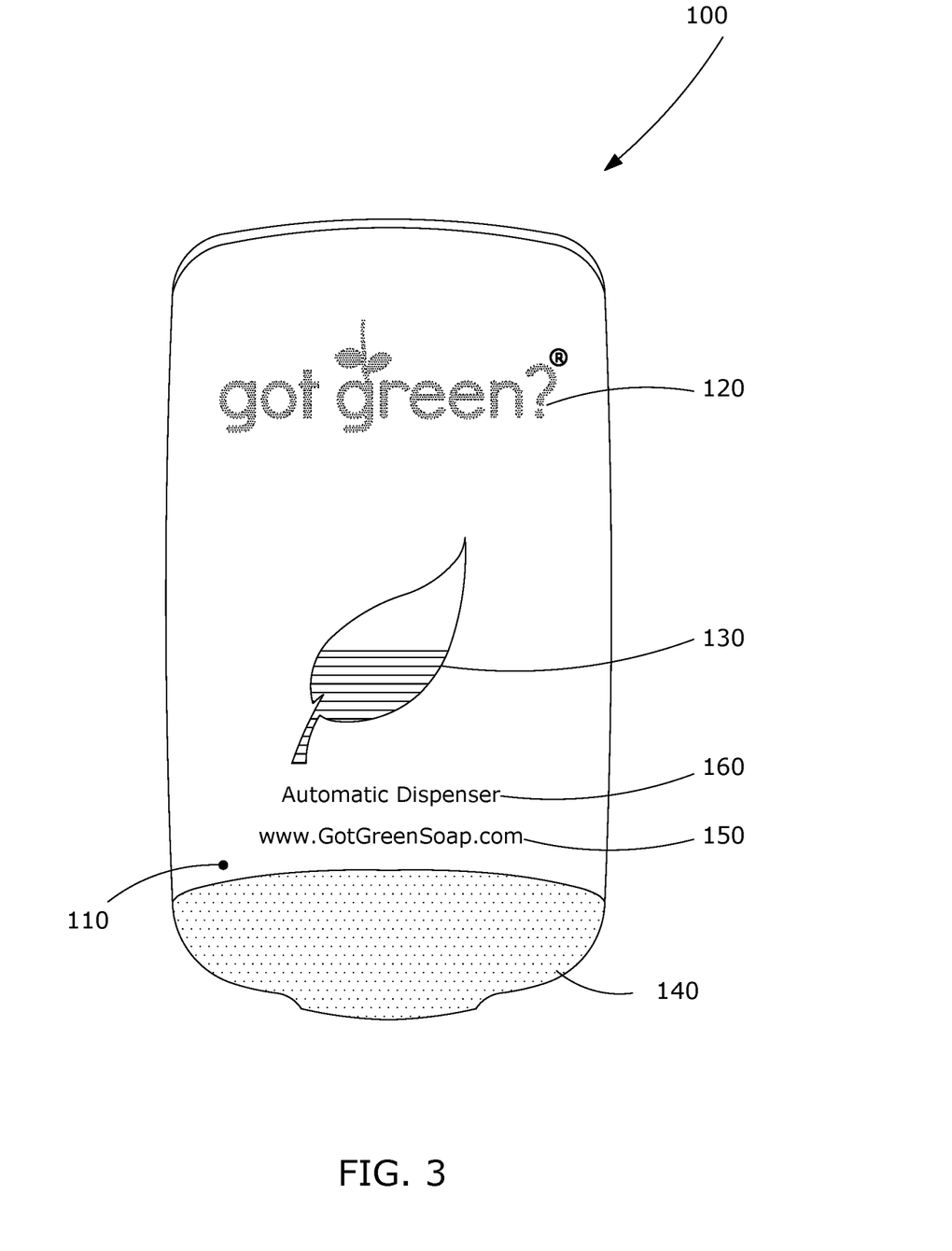
FIG. 3 is a front elevational view of an exemplary automatic foaming soap dispenser of the present disclosure.
Figure 4:
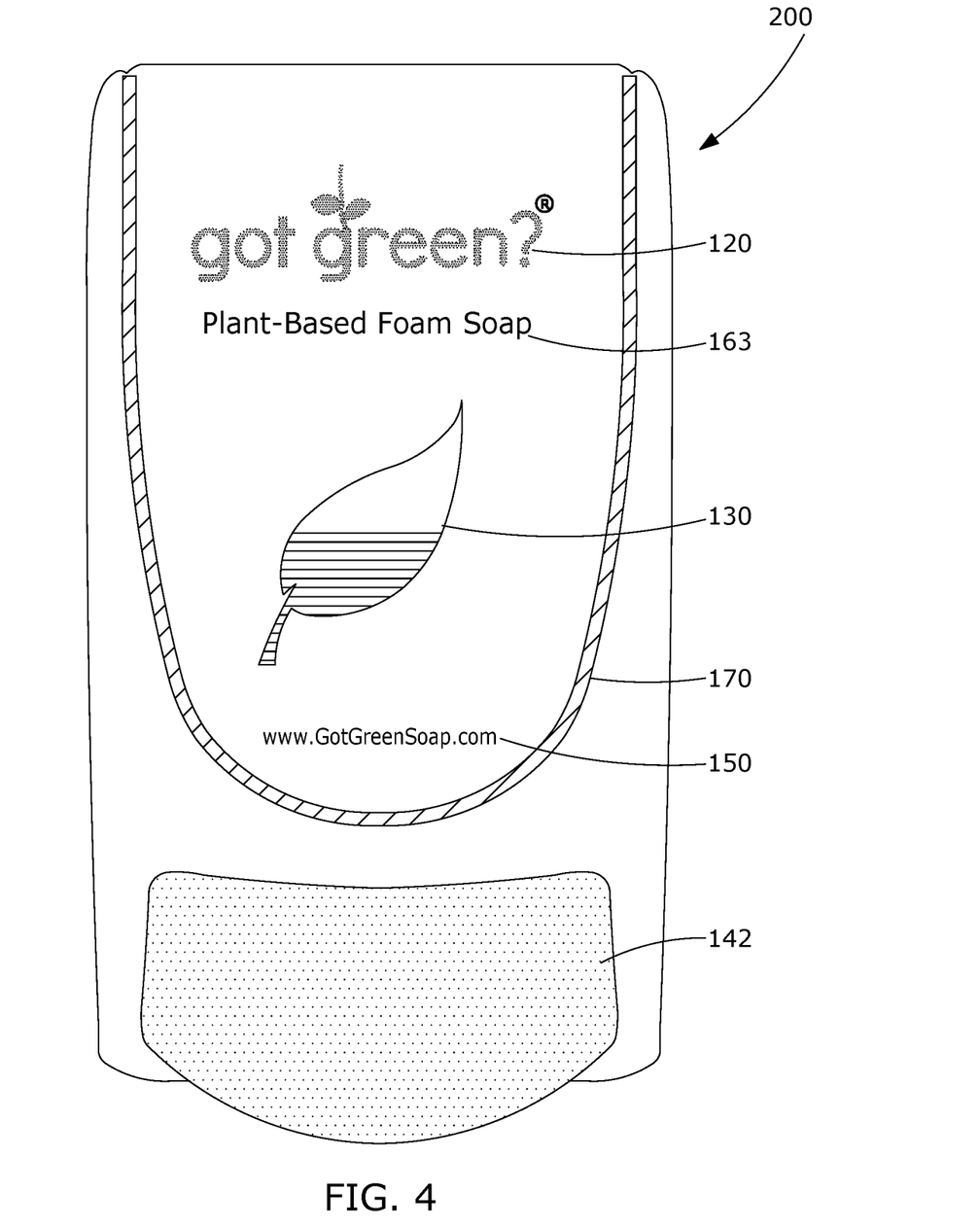
FIG. 4 is a front elevation view of an exemplary manual foaming soap dispenser of the present disclosure.
Figure 5:
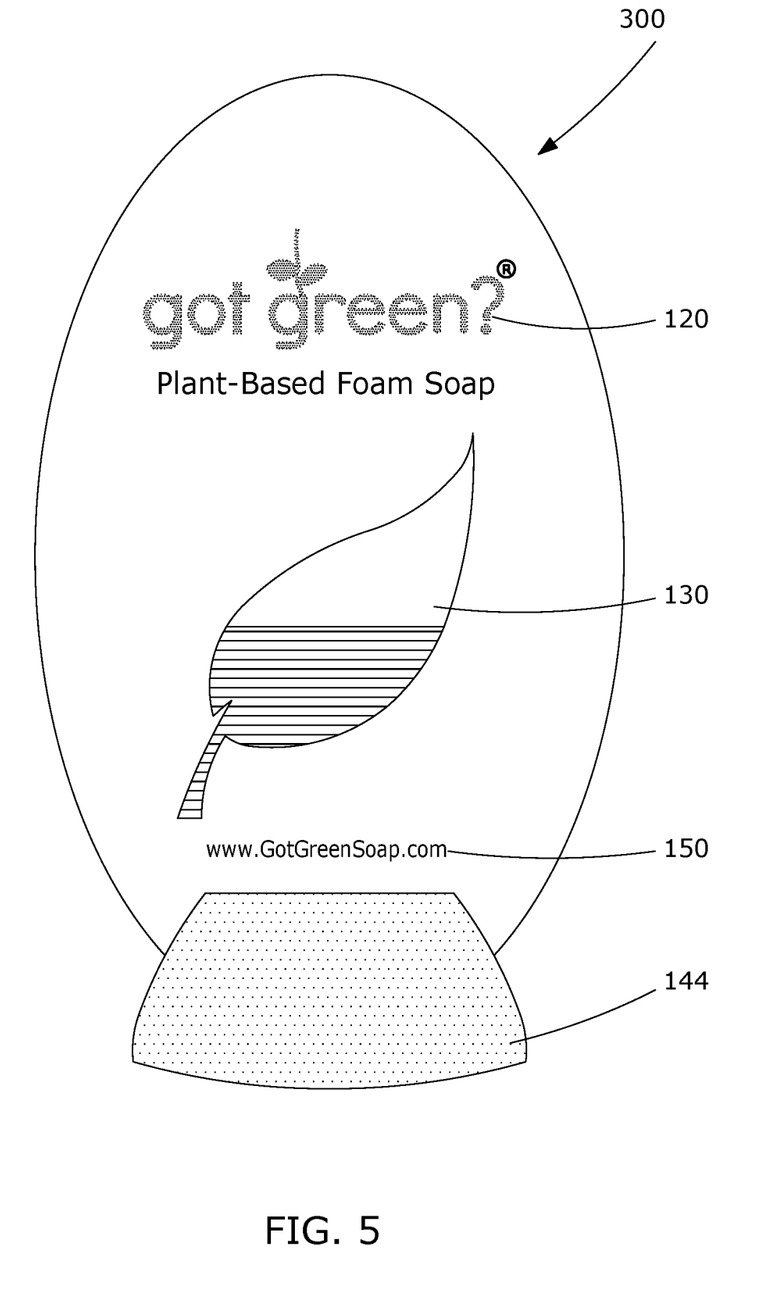
FIG. 5 is a front elevation view of another exemplary manual foaming soap dispenser of the present disclosure.
Figure 6:
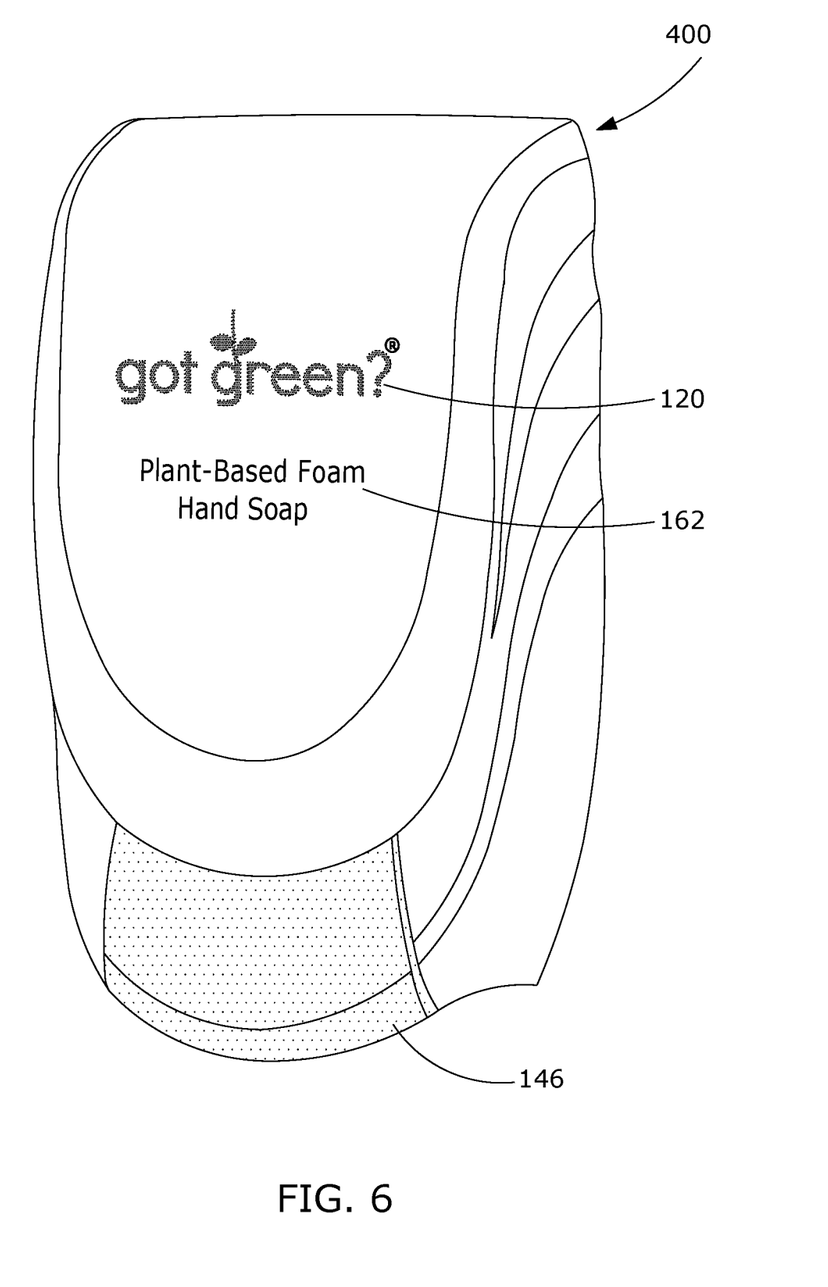
FIG. 6 is a front perspective view of a prior art manual foaming soap dispenser comprising the organic composition markings of the present disclosure.
Figure 7:
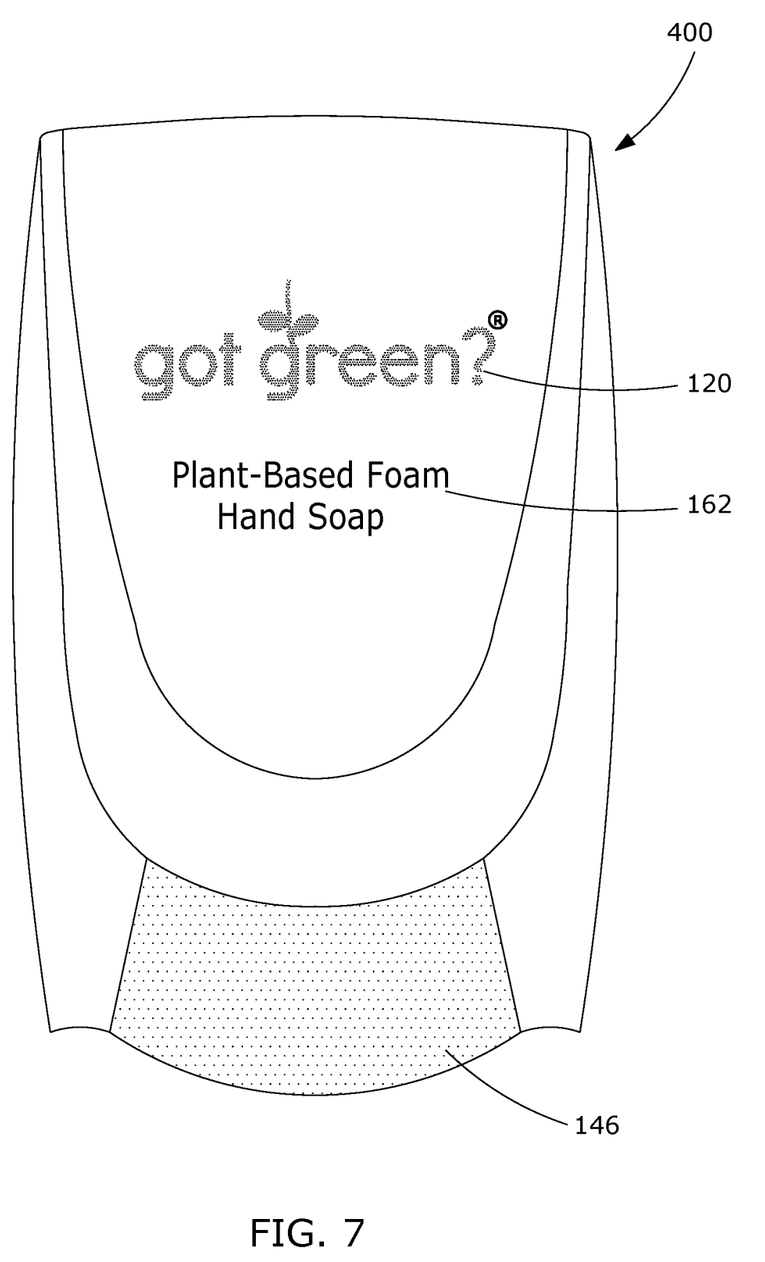
FIG. 7 is a front elevational view of the soap dispenser of FIG. 6.
Figure 8:
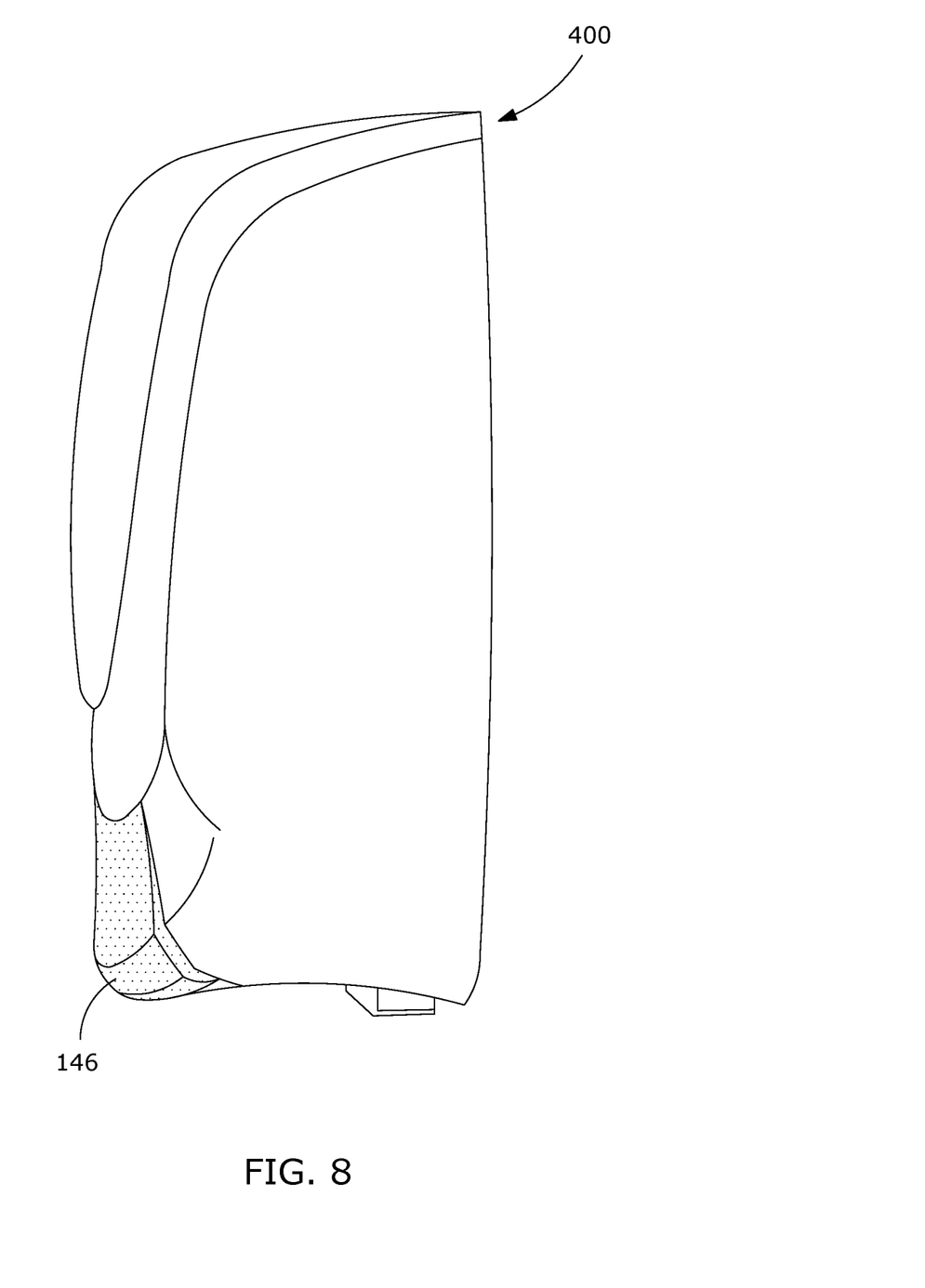
FIG. 8 is a right-side view of the soap dispenser of FIG. 6.
Figure 9:
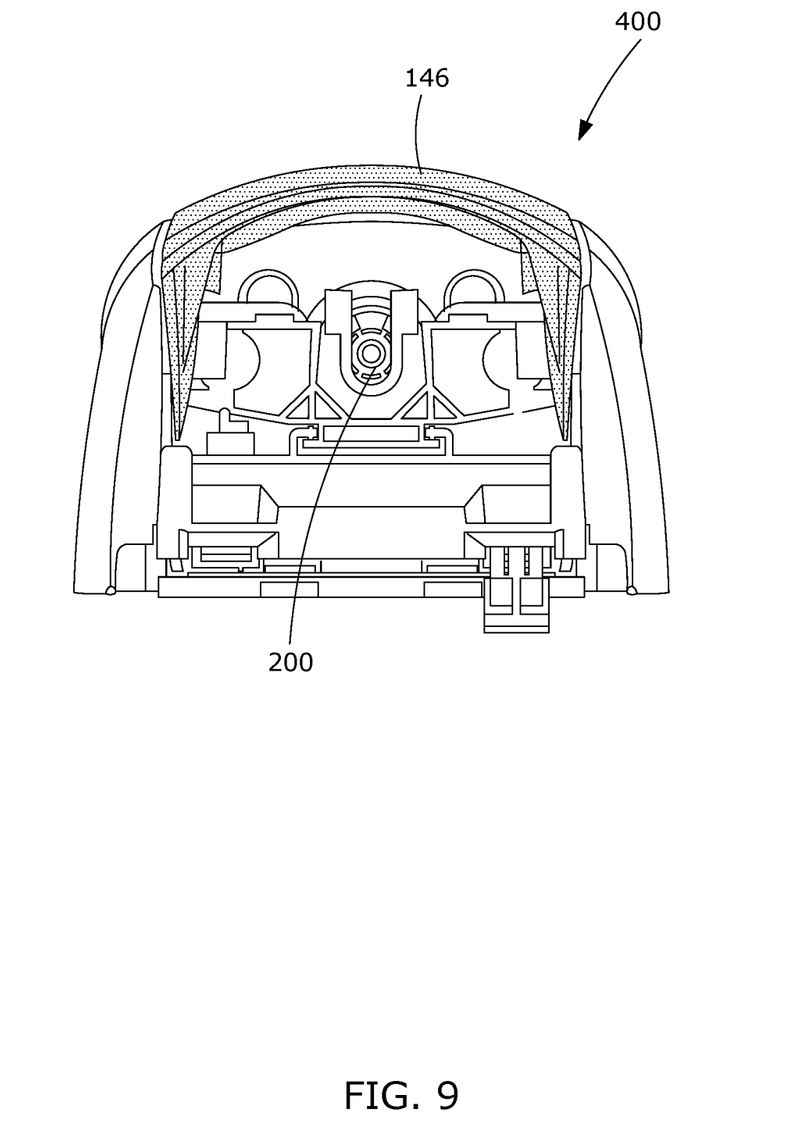
FIG. 9 is a bottom view of the soap dispenser of FIG. 6 that illustrates the foam dispensing nozzle.

As illustrated in FIGS. 3-5, the soap dispenser markings may further comprise a green, or partially green, colored leaf 130 on the front of the dispenser to indicate that the soap is plant-based.

Recyclable Dispenser: And in an embodiment, as illustrated in FIGS. 3-5, the entire dispenser, and the refillable or replaceable soap cartridge that it houses, are made entirely of recyclable plastic material, such polyethylene terephthalate (PET); high density polyethylene (HDPE); polyvinyl chloride; low density polyethylene (LDPE); polypropylene (PP); polystyrene (PS); ABS; and polyurethane.

Liquid Versus Foam Soap Dispensers

The soap compositions for the present disclosure are also housed in a soap dispenser that pumps out the soap in a liquid form, or as a foam, based upon the mechanical components of the dispenser. Foaming soap dispensers that mix the liquid soap with a gas, such as air or ozone, before dispensing are well known in the art, such as for air U.S. Pat. Nos. 6,409,050 B1; 8,091,739 B2; 8,113,388 B2; and 8,413,852 B2, to Ophardt et al.; and for ozone see US Patent Application 20130119083 A1 to Ophardt et al.

In an embodiment, as disclosed in U.S. Pat. No. 6,409,050 B1 to Ophardt et al., a pump assembly provides for direct replacement of volumes of the organic liquid soap from a reservoir with equal volumes of air preferably at substantially atmospheric pressure. A slide arrangement preferably positively displaces liquid from the soap reservoir and air into the soap reservoir. The pump draws air from the atmosphere into a chamber from which the air either is available for passage to replace liquid from the reservoir, or is pressurized to assist dispensing liquid soap, preferably, admixing with the liquid to provide foaming soap. Gravity separation of air and liquid to be dispensed is used to replace liquid with air in the reservoir and to selectively place air and liquid into communication with passageways for ejection.

In an embodiment, as illustrated in FIGS. 3-9, the soap dispenser comprises a rigid housing that is wall-mounted, in a substantially oval shaped (e.g. FIG. 5), or a substantially rectangular shape (FIGS. 3, 4, 6-8). In an embodiment, the rectangular-shaped embodiment dimensions comprise: 263 mm in height, 159 mm in width, and 101 mm in depth-thickness.

The dispenser further comprises a recyclable dispenser refill container holding the soap composition of the present disclosure. In an embodiment, the refill container is shaped to be about: 8.5 inches in height, 5.5 inches in width, and 3 inches in depth, and holds about 1000 mL of the soap composition, e.g. as per Table 1.

In another embodiment, the soap dispenser comprises a rigid housing that is affixed to, or within the sink, and adjacent to the faucet (e.g. see U.S. Pat. No. 8,991,657 to Ciavarella et al., and US Patent Application 20170027390 A1 to Maercovich, wherein the entire contents of both are incorporated by reference in its entirety).

In another embodiment, the soap dispenser is an over-the-counter, portable product comprising a collapsible housing made from a recyclable plastic that contains from about 12 to about 56 fluid ounces of the organic soap composition of the present disclosure. A pump action handle enables the user to push down to receive a unit of liquid or foaming organic soap with each pump.

Manual Versus Automatic Soap Dispensers

The dispensers of the present disclosure are also either automatic, so that the user does not need to touch the dispenser and risk receiving or transmitting germs (e.g. FIG. 3, dispenser 100), or manual (e.g. FIG. 4, dispenser 200; FIG. 5, dispenser 300; FIG. 6-9, dispenser 400), where the user pushes rearward (i.e. inward) on a bottom green colored tab (e.g. FIG. 4, 142; FIG. 5, 144; FIG. 6-9, 146). It is noted that the green tab 140 on the front of the automatic soap dispenser of FIG. 3 is for decorative purposes only, and it does not push inward.

Automatic Dispensers: Touchless, liquid and foaming, soap dispensers are well known in the art, such as U.S. Pat. No. 8,308,027 B2 to Law et al.; U.S. Pat. No. 6,390,329 B1 to J. T. Maddox; U.S. Pat. No. 7,281,643 B2 to P H Lin; and U.S. Pat. No. 5,492,247 to Shu et al. And the entire contents of these patents are hereby incorporated by references in their entireties. The automatic dispensers may further comprise markings on the dispenser to indicate "Automatic Dispenser", see FIG. 3, 160.

Automatic dispensers of the present disclosure comprise a sensor on the front of the dispenser that detects the user's hand (e.g. FIG. 3, 110), or on the bottom of the sensor near the nozzle. A variety of types of sensors are well known in the art for use in touchless dispensers, such as: photo, passive infrared, radar-based, motion, and proximity. Sensor activation triggers a motor to pump a premeasured amount of the soap from the bottom nozzle (e.g. see FIG. 9, 200).

The touchless dispenser of the present disclosure is powered by a rechargeable, or extended life battery, and/or a solar or incandescent light energy source.

Manual Activated Dispensers are well known in the art, and for use in the present disclosure generally comprise a wall-mounted housing with internal components and mechanisms comprising: a manually operable pumping means (e.g. green colored push tab FIG. 4, 142; FIG. 5, 144; FIGS. 6-9, 146), and a liquid soap filled reservoir that is operatively connected to the pumping means for supplying soap to be dispensed via a vertically mounted tube extending between the reservoir and a dispenser nozzle with a close/open valve.

Exemplary manual activated dispensers for use with the housings of FIGS. 3-9 for dispensing premeasured amounts of the liquid or foam organic soap composition of the present disclosure comprise, for example, U.S. Pat. No. 6,086,162 to De Winter et al.; U.S. Pat. Nos. 6,409,050 B1; 8,091,739 B2; 8,113,388 B2; and 8,413,852 B2, to Ophardt et al.

Replaceable Soap Cartridge: The dispensers further comprise a removeable dispenser cartridge for the user to easily replace the soap reservoir when it is empty. For example, U.S. Pat. Nos. 8,091,739 B2; 8,113,388 B2; and 8,413,852 B2, to Ophardt et al., disclose a soap dispenser with a pump piston for both liquid and foaming soap that provides a replaceable liquid soap reservoir.

CONCLUSION

As used herein, "substantially" refers to possible relatively small deviations (if any) of the stated shape.

Other features that are considered as characteristic for the various embodiments are set forth in the appended claims.

Although the various embodiments are illustrated and described herein as embodied in organic soap compositions and dispensers, it is nevertheless not intended to be limited to the details shown, since various modifications and structural changes may be made therein without departing from the spirit of the invention and within the scope and range of equivalents of the claims.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as an "aspect" may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as a "configuration" may refer to one or more configurations and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology.

LIST OF REFERENCES CITED

1) Genena A K; Hense H; Junior A S; de Souza S M. "Rosemary (*Rosmarinus officinalis*)—a study of the composition, antioxidant and antimicrobial activities of extracts obtained with supercritical carbon dioxide," Food Science and Technology, April/June 2008; 28(2): 463-469.
2) Al-Hijazeen M, Al-Rawashdehi M. "Preservative effects of rosemary extract (*Rosmarinus officinalis L.*) on quality and storage stability of chicken meat patties," Food Sci. Technol, ahead of print Epub Nov. 13, 2017.
3) Shahbazi Y. "Chemical Composition and In Vitro Antibacterial Activity of *Mentha spicata* Essential Oil against Common Food-Borne Pathogenic Bacteria," J Pathog. 2015; 1-5.
4) Shahbazi Y, Karami N, Shavisi N. "Effect of *Mentha spicata* essential oil on chemical, microbial, and sensory properties of minced camel meat during refrigerated storage," February 2018; 38(1): 1-7.
5) Sowndhararajan K, Kim S. "Influence of Fragrances on Human Psychophysiological Activity: With Special Reference to Human Electroencephalographic Response," Sci Pharm. 2016; 84(4): 724-752.
6) Bhandari S S, Kabrab M P. "To evaluate anti-anxiety activity of thymol," Journal of Acute Disease. 2014, 3(2): 136-140.
7) Priestley C M, Williamson E M, Wafford K A, and Sattelle D B. "Thymol, a constituent of thyme essential oil, is a positive allosteric modulator of human GABAA receptors and a homo-oligomeric GABA receptor from Drosophila melanogaster," Br J Pharmacol. 2003 December; 140(8): 1363-1372.
8) Lockette T. "Florida researchers use essential oil as earth-friendly pesticide," SouthEast FarmPress, Apr. 21, 2004.
9) EPA Red Facts, Thymol, EPA-738-F-93-010, September 1993.
10) T M Nalawade, K Bhat, SHP Sogi, "Bactericidal activity of propylene glycol, glycerine, polyethylene glycol 400, and polyethylene glycol 1000 against selected microorganisms," J Int Soc Prey Community Dent. 2015 March-April; 5(2): 114-119.

OTHER CITED REFERENCES

U.S. Pat. No. 6,409,050 B1 that issued Jun. 25, 2002 to Ophardt et al.
U.S. Pat. No. 8,091,739 B2 that issued Jan. 10, 2012 to Ophardt et al.
U.S. Pat. No. 8,113,388 B2 that issued Feb. 14, 2012 to Ophardt et al.
U.S. Pat. No. 8,413,852 B2 that issued May 16, 2013 to Ophardt et al.
U.S. Pat. No. 8,308,027 B2 that issued Nov. 13, 2012 to Law et al.
U.S. Pat. No. 6,390,329 B1 that issued May. 21, 2002 to J. T. Maddox.
U.S. Pat. No. 7,281,643 B2 that issued Nov. 16, 2007 to P H Lin.
U.S. Pat. No. 5,492,247 that issued Feb. 20, 1996 to Shu et al.

U.S. Pat. No. 8,991,657 that issued Mar. 31, 2015 to Ciavarella et al.

U.S. Pat. No. 6,068,162 that issued May 30, 2000 to De Winter et al.

US Patent Application 20130119083 A1 that issued May 16, 2013 to Ophardt et al.

US Patent Application 20170027390 A1 that issued Feb. 2, 2017 to Maercovich.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the scope of the appended claims.

What is claimed is:

1. An organic, plant-based moisturizing anti-microbial hand soap composition comprising,
    a) a base soap, comprising: saponified organic coconut oil; saponified organic olive oil; saponified organic sunflower oil; saponified organic jojoba oil; and organic aloe vera, wherein said base soap comprises about 90.80 wt. % of the composition;
    b) a plurality of anti-microbial active ingredients comprising: organic shea butter; organic spearmint oil; USDA approved lime oil; organic thyme oil; and organic rosemary extract;
    wherein said composition does not comprise sulfites, non-organic plant-based chemicals, or synthetic compounds;
    wherein said composition is effective as a moisturizing antimicrobial soap, a leave-on non-sticky hand sanitizer, and an air freshener by absorbing and reducing odor causing airborne bacteria; and
    wherein the composition is able to eradicate about 74.6% through 77.6% of the bacterial strain *Staphylococcus aureus* after at least one minute of direct contact with the composition.

2. The organic plant-based moisturizing anti-microbial hand soap composition of claim 1, further comprising glycerin as an anti-microbial active ingredient in an amount of about 1 wt. % to about 15 wt. %.

3. The organic plant-based moisturizing anti-microbial hand soap composition of claim 1, wherein said composition is in a liquid or foam formulation after dispensing.

4. The organic plant-based moisturizing anti-microbial hand soap composition of claim 1, wherein the organic shea butter is in a range from about 0.50 weight % to about 5.0 weight %.

5. The organic plant-based moisturizing anti-microbial hand soap composition of claim 1, wherein the organic spearmint oil is in a range from about 0.42 weight % to about 0.7 weight %.

6. The organic plant-based moisturizing anti-microbial hand soap composition of claim 1, wherein the USDA approved lime oil is in a range from about 0.44 weight % to about 0.66 weight %, and is USDA approved.

7. The organic plant-based moisturizing anti-microbial hand soap composition of claim 1, wherein the organic thyme oil is in a range from about 0.07 weight % to about 0.11 weight %.

8. The organic plant-based moisturizing anti-microbial hand soap composition of claim 1, wherein the organic rosemary extract is in a range from about 0.01 weight % to about 0.13 weight %.

9. The organic plant-based moisturizing anti-microbial hand soap composition of claim 1, wherein the shelf-life of the composition is about three years.

10. The organic plant-based moisturizing anti-microbial hand soap composition of claim 1, wherein the organic hand soap composition is convertible from a liquid soap to a foaming soap by a wall-mounted, automatic or manual soap dispenser comprising: a pumping means able to mix air with the liquid soap within the dispenser to produce a foaming soap.

11. A foam producing plant-based moisturizing anti-microbial hand soap product comprising:
    a) a foam-able organic, plant-based liquid soap composition comprising:
        a base soap, comprising: saponified organic coconut oil; saponified organic olive oil;
        saponified organic sunflower oil; saponified organic jojoba oil; and organic aloe vera, wherein said base soap comprises about 90.80 wt. % of the composition;
        a plurality of anti-microbial active ingredients comprising: organic shea butter; organic spearmint oil; USDA approved lime oil; organic thyme oil; and organic rosemary extract;
    b) a foam hand soap dispenser for dispensing the organic liquid soap composition as a premeasured amount of foaming soap, wherein the foam dispenser comprises: a recyclable plastic; a bottom front tab comprising a green color and a front label indicating the composition is an plant-based, organic soap;
    wherein said composition does not comprise sulfites, non-organic plant-based chemicals, or synthetic compounds;
    wherein said composition is effective as a moisturizing antimicrobial soap, a leave-on non-sticky hand sanitizer, and an air freshener by absorbing and reducing odor causing airborne bacteria; and
    wherein the composition is able to eradicate about 74.6% through 77.6% of the bacterial strain *Staphylococcus aureus* after at least one minute of direct contact with the composition.

12. The foam producing hand moisturizing anti-microbial hand soap product of claim 11, wherein the foam soap dispenser is a manual soap dispenser comprises comprising a manually operable pumping means that mixes air with the liquid soap within the dispenser to produce a foaming soap.

13. The foam producing moisturizing anti-microbial hand soap product of claim 12, wherein the foam soap dispenser further comprises a liquid soap filled reservoir that is operatively connected to the pumping means for supplying the organic soap composition to the dispenser via a vertically mounted tube extending between the reservoir and a dispenser nozzle connected to a close/open valve.

14. The foam producing moisturizing anti-microbial hand soap product of claim 11, wherein the organic soap composition further comprises glycerin as an ingredient in an amount of about 1 wt. % to about 15 wt. %.

15. The foam producing moisturizing anti-microbial hand soap product of claim 11, wherein the shelf-life of the organic soap composition is about three years.

16. A foam producing moisturizing anti-microbial hand soap product comprising:
   a) a foam-able organic, plant based, liquid soap composition comprising the base soap ingredients of:
      saponified organic coconut oil; organic olive oil; organic sunflower oil; organic jojoba oil; and organic aloe vera, wherein said base soap comprises about 90.80 wt. % of the composition;
      a plurality of anti-microbial ingredients comprising organic shea butter and organic rosemary extract;
   b) a foam hand soap dispenser for dispensing the organic liquid soap composition as a premeasured amount of foaming soap, wherein the foam dispenser comprises: a recyclable plastic; a bottom front tab comprising a green color and a front label indicating the composition is an organic soap;
   wherein said composition does not comprise sulfites, non-organic plant-based chemicals, or synthetic compounds; and
   wherein said composition is effective as: a moisturizing antimicrobial leave-on, non-sticky hand sanitizer; and an air freshener by absorbing and reducing odor causing airborne bacteria.

17. The foam producing hand soap product of claim 16, wherein the foam soap dispenser is a manual soap dispenser comprising a manually operable pumping means that mixes air with a liquid soap within the dispenser to produce a foaming soap.

18. The foam producing hand soap product of claim 16, wherein the organic soap composition further comprises glycerin as an ingredient in an amount of about 1 wt. % to about 15 wt. %.

19. The foam producing hand soap product of claim 16, wherein the organic soap composition further comprises at least one organic essential scented oil, or any combination thereof: orange essential oil, lemon essential oil, lime essential oil, citrus blend essential oil, kiwi oil, strawberry essential oil, raspberry essential oil, elderberry essential oil, juniper berry essential oil, cranberry essential oil, pomegranate essential oil, vanilla essential oil, lemongrass essential oil, rosemary essential oil, patchouli essential oil, thyme essential oil, spearmint essential oil, peppermint essential oil, wintergreen essential oil, cinnamon bark and leaf essential oil, sage essential oil, basil essential oil, sweet basil essential oil, pine blend essential oil, frankincense essential oil, ginger essential oil, mandarin essential oil, tangerine essential oil, grapefruit essential oil, floral fragrance, lavender essential oil, rose essential oil, *gardenia* essential oil, geranium essential oil, sweet marjoram oil, nutmeg essential oil, bergamot essential oil, cardamom essential oil, chocolate fragrance oil, and coconut fragrance oil.

20. The foam producing moisturizing antimicrobial hand soap product of claim 11, wherein the foam hand soap dispenser is a wall-mounted hand soap dispenser.

21. The foam producing moisturizing antimicrobial hand soap product of claim 16, wherein the foam hand soap dispenser is a wall-mounted hand soap dispenser.

* * * * *